United States Patent [19]
Beaty et al.

[11] Patent Number: 5,366,412
[45] Date of Patent: Nov. 22, 1994

[54] TORQUE LIMITING CLUTCH AND ITS USES

[75] Inventors: Keith D. Beaty, West Palm Beach; Dan P. Rogers, Royal Palm Beach, both of Fla.

[73] Assignee: Implant Innovations, Inc., West Palm Beach, Fla.

[21] Appl. No.: 885,619

[22] Filed: May 19, 1992

[51] Int. Cl.$^5$ .......................... F16D 7/04; A61C 8/00
[52] U.S. Cl. ............................. 464/38; 464/37; 464/34; 433/173; 433/174
[58] Field of Search .................. 464/39, 38, 37, 35, 464/36; 433/173, 174; 192/56 R

[56] References Cited

U.S. PATENT DOCUMENTS

| | | | |
|---|---|---|---|
| 1,126,219 | 1/1915 | Hupp | 464/38 |
| 2,275,004 | 3/1942 | Behl | 464/39 |
| 2,806,366 | 9/1957 | Woestemeyer | 464/36 |
| 2,818,712 | 1/1958 | Barnes et al. | 464/36 |
| 2,927,672 | 3/1960 | Banner | 464/39 |
| 3,205,985 | 9/1965 | Pearl | 192/56 R |
| 3,942,337 | 3/1976 | Leonard et al. | 464/36 |
| 4,850,567 | 7/1989 | Ambrosi | 464/36 |

FOREIGN PATENT DOCUMENTS

| | | | |
|---|---|---|---|
| 808545 | 2/1959 | United Kingdom | 464/38 |
| 530125 | 9/1976 | U.S.S.R. | 464/39 |

*Primary Examiner*—Clifford D. Crowder
*Assistant Examiner*—Bibhu Mohanty
*Attorney, Agent, or Firm*—Alfred H. Rosen

[57] ABSTRACT

A torque limiting clutch which transmits gradually increasing torque up to a prescribed limit at which limit the clutch disengages from its load. An embodiment designed for light service use in dentistry encloses all the working parts in a housing through which torque is applied to the load, and is autoclavable. This embodiment can be attached to known dental headpieces for assembling components of dental restorations with prescribed limited torque.

41 Claims, 9 Drawing Sheets

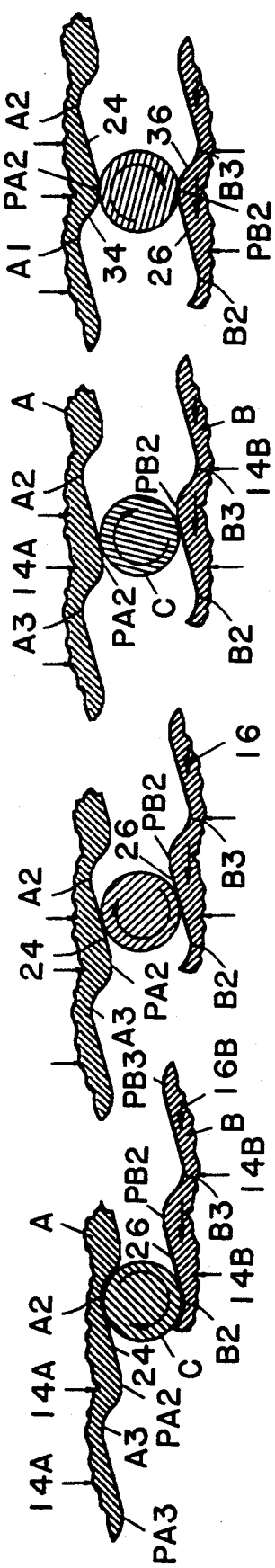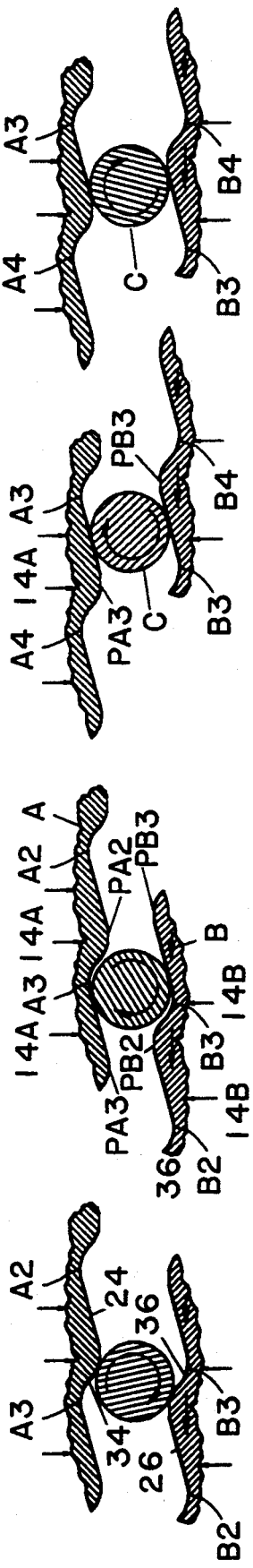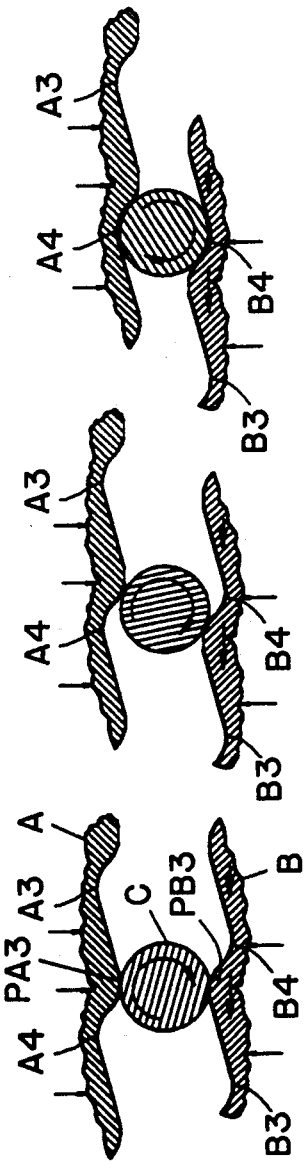

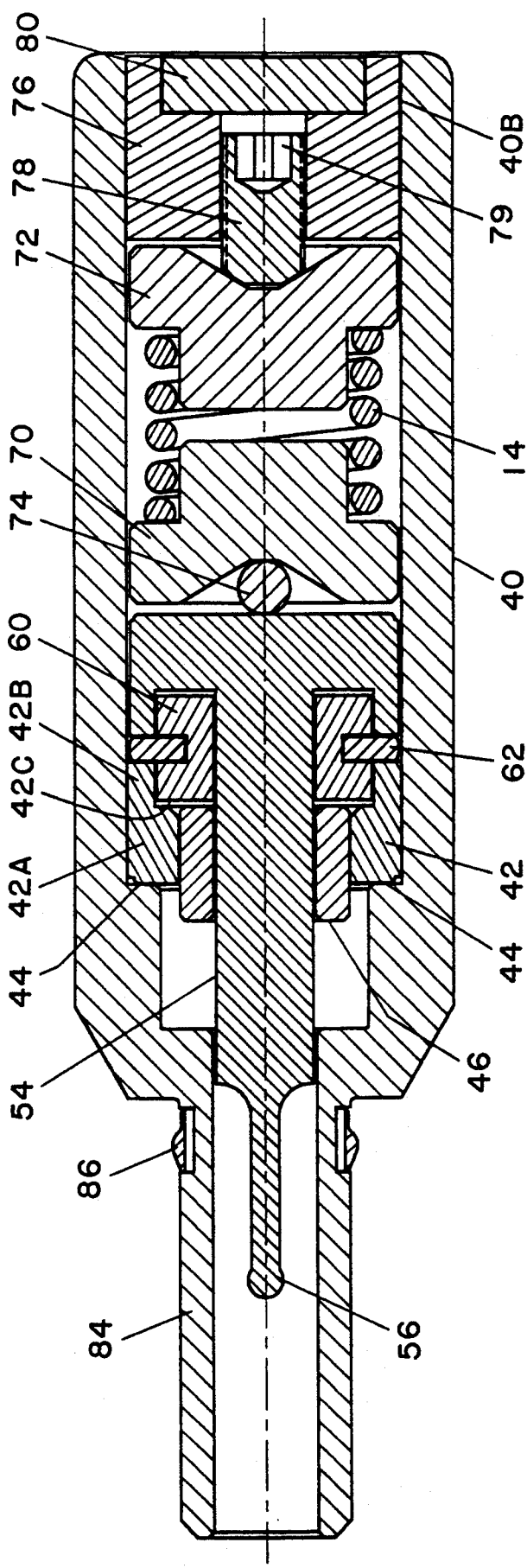
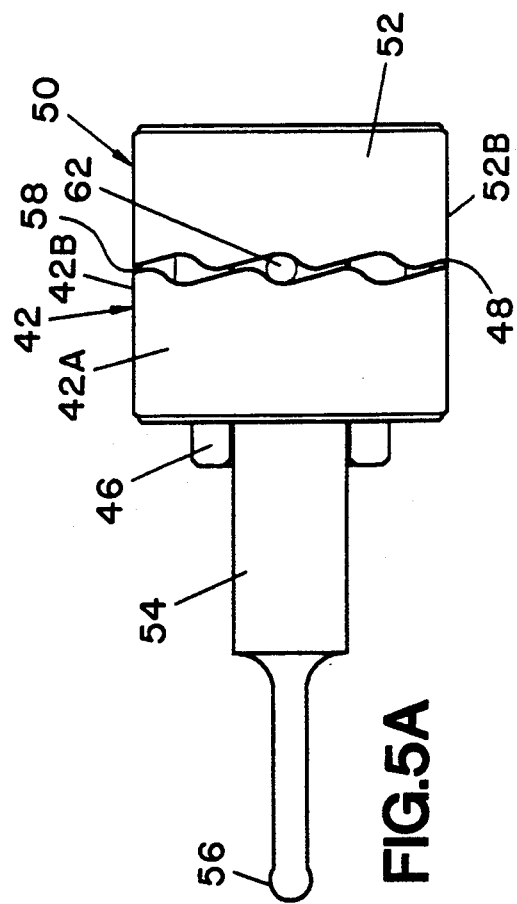
FIG.5
FIG.5A

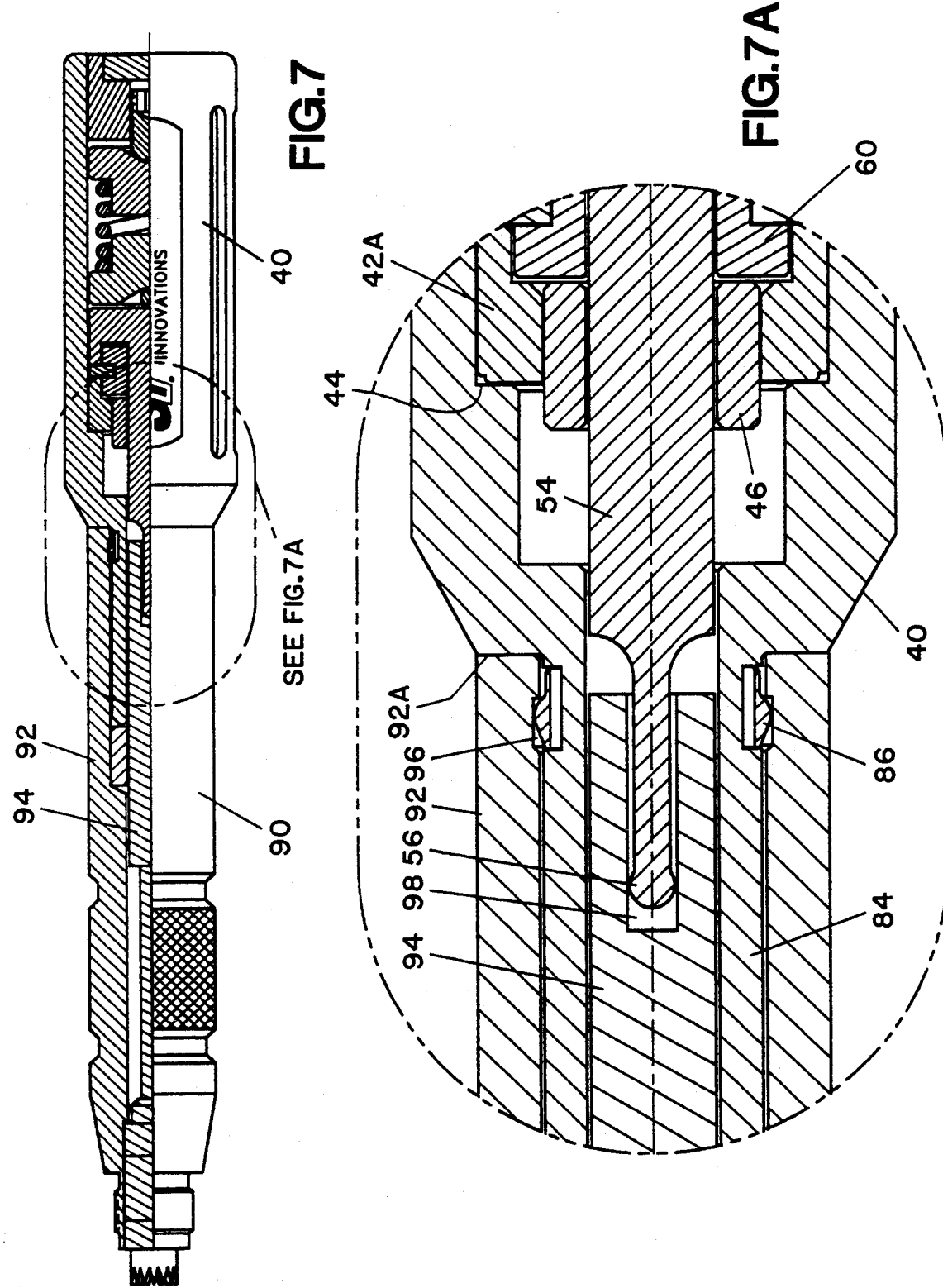

TORQUE LIMITING CLUTCH AND ITS USES

This invention relates to a new torque limiting clutch and its uses in a wide variety of applications including applications in dental and medical environments where such devices have not heretofore been suitable for use. To this end the invention further relates to torque limiting clutches which require no lubricant and can be sterilized by available means such as autoclaving.

BACKGROUND OF THE INVENTION

Improvements in the field of dental implantology have given restorative dentists and their partially or wholly edentulous patients the increasing option to support new artificial teeth on artificial roots. Prominent among the artificial roots that have become available is the osseointegrated dental implant fixture; commonly, this fixtures takes a cylindrical form which is implantable in the patient's jawbone and has an axially located internally-threaded bore for receiving an externally threaded bolt which is used to attach to the implant fixture an artificial tooth, or an intermediate component between the fixture and the tooth. In practice one or more such bolts may be used to attach one tooth to an artificial root. The artificial tooth itself is frequently built on, or includes in its structure, a component which is designed and intended for cooperation with such a bolt. Thus, threaded bolts are important subcomponents in the structures of artificial teeth in a dental restoration supported on a dental implant fixture or fixtures.

With experience has come the realization that the bolts used in such dental restorations may have certain critical properties. The implant fixtures and the components assembled on them are made of materials chosen for suitability in dental use; presently the metal titanium is the material of choice. The bolts may suitably but not necessarily be made of gold. These are not hard metals such as steel that are commonly used in industrial structures, yet the bolts must be tightened enough so that the restored dentition will not fail in use. Attention has been given to designing and making the implant fixtures and related components to a high degree of dimensional precision and repeatability to minimize the opportunity of components to rock against each other and the implant fixture and thereby bending the attaching bolts and eventually breaking them. And, more recently, attention has been given to tightening the bolts just enough so that they will hold all the assembled parts tightly together throughout the range of forces those parts will encounter in use, but not so much that the bolts will be stretched beyond their elastic limit and break. The small sizes in which these bolts are made, as low as 1/16th of an inch, and generally not more than ⅛th of an inch in diameter at the peaks of their threads, have made this a critical and burdensome problem. To respond to the problem some tool manufacturers have provided complicated machines for controlling the torque applied to the bolts during assembly of the teeth and components on dental implant fixtures. Such machines that are currently available employ cabinets enclosing complex electronic motor control circuitry, a motor-driven handpiece for holding and driving a screwdriver bit, and a long flexible cable connecting the handpiece to the cabinet. Along with all this gadgetry is a group of settable controls on the cabinet and a handbook telling the dentist how to operate and maintain the equipment, and, of course, a correspondingly-high price.

GENERAL NATURE OF THE INVENTION

The present invention provides a torque-limiting clutch having a driving member and a driven member, each member with a confronting clutch surface having on it a periodic wave of like frequency to the other confronting surface, the two members being held with their confronting clutch surfaces facing each other, and means to apply a compressive force urging the two surfaces toward each other. The wave pattern of each cycle in each periodic wave has a slope rising gradually from its dwell to a peak followed by a drop to the dwell at the beginning of the next-following slope, to the end that when a driving torque is applied to the driving member the torque transmitted to the driven member will increase gradually to a limit determined in part by the magnitude of the compressive force and in part by the steepness of the slopes of the sides of the confronting wave patterns that are engaged in transmitting the torque from the driving member to the driven member. By choosing a wave pattern having a steeper slope on one side than on the other side one can achieve a clutch according to the invention which will have a first torque limit when driving torque is applied in one direction that is larger than the torque limit reached when driving force is applied in the other direction. This feature of the invention makes possible the provision of a single tool which can apply a safely limited torque for driving a bolt and a larger limited torque for removing it, should its removal become necessary.

In the field of restorative dentistry incorporating dental implant fixtures and components as described above the torque forces applied to the connecting bolts are small, measured in Newton-centimeters (Ncm), and it is highly desirable that a torque-limited driver for use in driving such bolts be accurate to within approximately plus or minus one Ncm. from an original pre-set calibration of the tool. To aid in achieving this degree of precision this new clutch includes mechanical anti-friction means between the confronting clutch surfaces which requires no lubrication. In addition, a substantially flat surface is provided at the peak of each cycle, and the flat surfaces of each member lie in the locus of a common plane, and the planes of the driving and driven members are parallel to each other, all to assured that the torque limit of the clutch will be as near as possible the same from one cycle of the periodic wave of each member to the next.

An embodiment of the invention suitable for use in dentistry features a unitary housing enclosing the driving member, the driven member, an assembly of roller bearings between the confronting wave surfaces, a unit for applying the compressive force and means to pre-set the magnitude of the compressive force in Ncm. The housing and its entire contents are without any lubricant, and are completely autoclavable. The driving member is fixed in the housing, and the driven member is held free to rotate within the housing when the pre-set torque limit is reached. The driven member has a coupling element extending from it for coupling with a tool for driving screws, bolts, nuts and the like. The housing is arranged to couple with such a tool so that rotation of the housing relative to the tool will transmit torque to the tool via the driven member. A set of torque-limited clutches, each precalibrated to a specific torque value, may be supplied for use with one tool.

When during use of the clutch the pre-set torque limit is reached a mechanical shock may be imposed on the coupling element of the driven member. Coupling between the coupling element and the tool is designed so that such shock, if present in the clutch assembly, is not transmitted to the tool. The tool experiences only a substantially instantaneous drop-off of driving torque when the pre-set torque limit is reached. This feature of the invention both protects the screw that is being driven and shields the patient from discomfort.

The invention is described in greater detail with reference to the accompanying drawings. These drawings include illustration of an embodiment of the invention that is suitable for use in dentistry, but the invention is not limited to details of that embodiment. It is intended and understood that this invention is applicable, and the scope of the appended claims extends to, all uses where it is desired to tighten, or to loosen, a screw, bolt, nut or the like with limited torque.

BRIEF DESCRIPTION OF THE DRAWINGS

FIGS. 3-1 through 3-11 constitute a flow diagram illustrating performance of the invention over a complete wave-cycle;

FIG. 4 is an isometric view illustrating incorporation of caged roller bearings in the invention;

FIG. 5 is an axial section through a torque limiting clutch of the invention enclosed in a housing;

FIG. 5A is a side view of the clutch components shown in FIG. 5;

FIG. 6 is an exploded view of FIG. 5;

FIG. 7 is a longitudinal view, partly in section, showing the clutch of FIG. 5 coupled to a dental handpiece of known configuration; and FIG. 7A is an expanded view of a portion of FIG. 7 showing details of the coupling between the clutch and the handpiece; and FIG. 8 shows another embodiment of the invention.

DETAILED DESCRIPTION OF THE DRAWINGS

Figure 1:
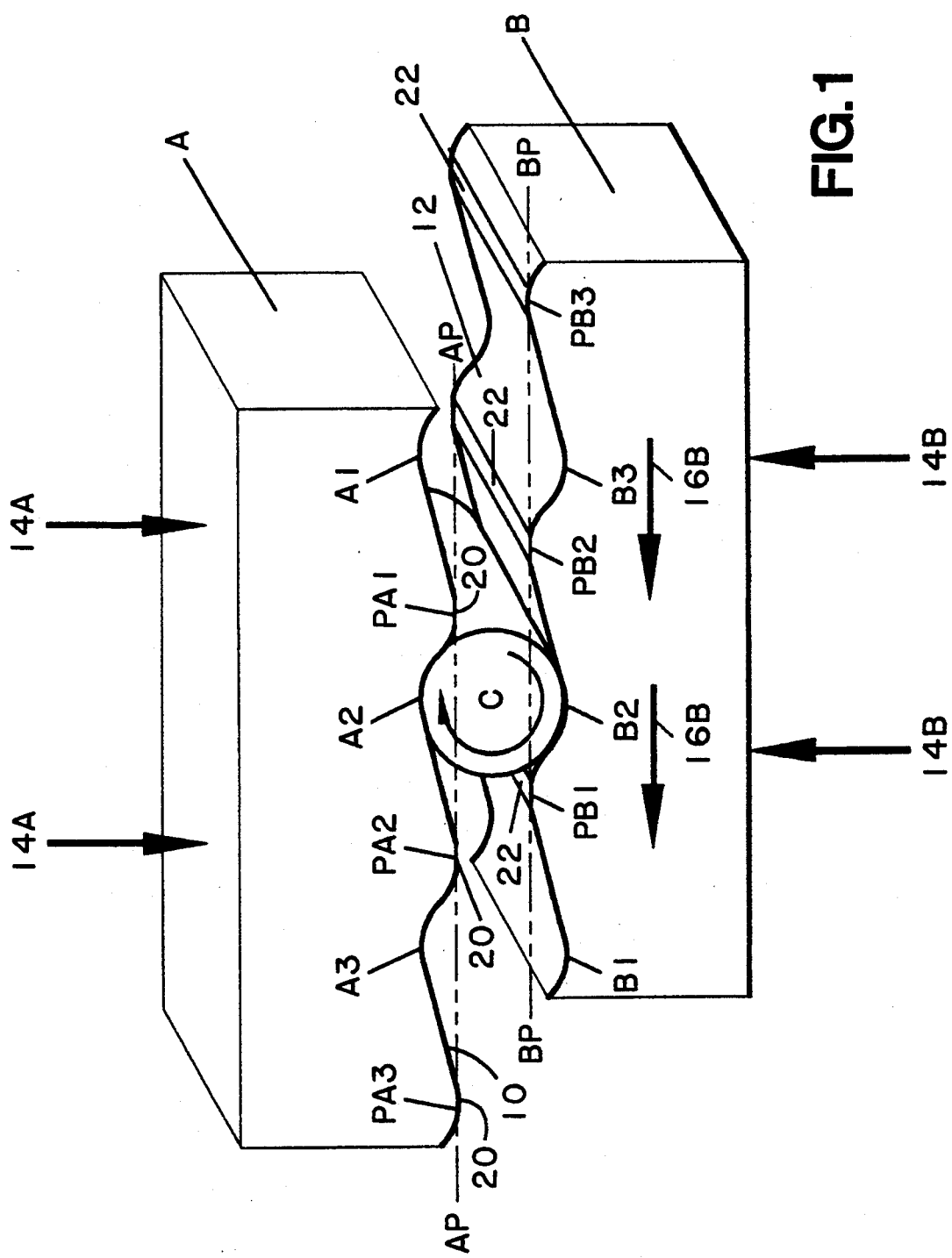
FIG. 1 is an isometric view illustrating basic principles of the invention.

In FIG. 1 a driven member A and a driving member B have confronting clutch surfaces 10 and 12, respectively, confronting each other, with an anti-friction roller C between them. A compressive force urging the two members together is represented by arrows 14A and 14B. A torque force applied to the driving member B in the direction of arrows 16B will move the driven member A in the same direction if the driven member does not resist, owing to the periodic wave-form shape of each surface 10 and 12. Three cycles of the wave form on each surface are shown; they are alike in frequency, period, and wave pattern, so that in the absence of the roller C the two confronting surfaces could nest together substantially uniformly. For convenience, the dwells in the wave form of the driving member B are labelled B1, B2 and B3, and the peaks are labelled PB1, PB2 and PB3. Likewise, on the driven member A the dwells are labelled A1, A2 and A3, while the peaks are labelled PA1, PA2 and PA3. FIG. 1 shows the torque limiting clutch in its rest position, as when no torque force is applied; in this position the roller C is nested between two dwells A2 and B2, and the two members A and B are as close to each other as they can be.

For purposes to be presently explained, each wave surface has a flat portion, 20 in driven member A and 22 in driving member B, at each peak. The flat portions 20 are in a common plane AP—AP, and the flat positions 22 are in a second common plane BP—BP, and these two planes are substantially parallel to each other.

The individual wave forms, as shown in this embodiment of the invention, are asymmetrical. Thus, referring to a single wave form B3 near the right-hand end of the driving member (as seen in the drawing), the segment of the wave form between its dwell B3 and its peak PB3 has a relatively gradual slope, whereas the remaining sector between the dwell B3 and the next succeeding peak PB2 has a shorter and relatively steeper slope. With this structure incorporated in its design, the torque-limiting clutch of the invention can have one value of torque limit when driven in one direction, and a different value of torque limit when driven in the opposite direction.

Figure 2:
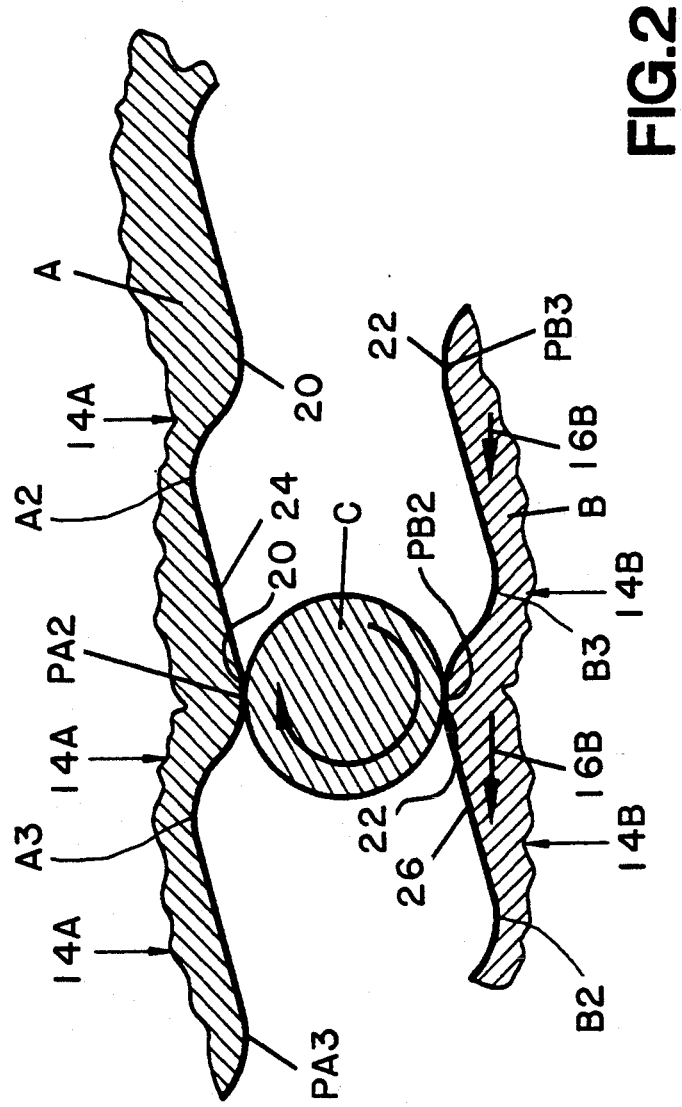
FIG. 2 is a sectional view illustrating the torque-release performance of the invention.

FIG. 2 illustrates the configuration of the driving and driven members B and A, respectively, at the moment of torque release, when the driving member looses driving connection with the driven member. Assume that the torque force represented by the arrows 16B has been resisted by the driven member A against the compressive force represented by arrows 14A and 14B, the driving member B slipping past the driven member A forces the roller C to roll out of the dwells B2 and A2 and to roll "up" the slope 24 leading to the following wave peak PA2, and "up" the slope 26 leading to the following wave peak PB2, until if resistance of the driven member A exceeds the pre-set torque limit the roller C is brought to a position between two confronting flat portions 20 and 22. This is the position of torque limit, in which the driving member B can no longer drive the driven member A. Following this event, the driving member B is decoupled from the driven member A and continues to move in the direction of arrows 16B until the roller C is forced ("falls") into the next pair of dwells A3 and B3 under the compressive force 14A and 14B, at which point the driven member A is again coupled to the driving member B, and driving torque is regained. When torque is lost the distance between the two members reaches a maximum, and that distance reaches a minimum when torque is regained.

Figure 4:
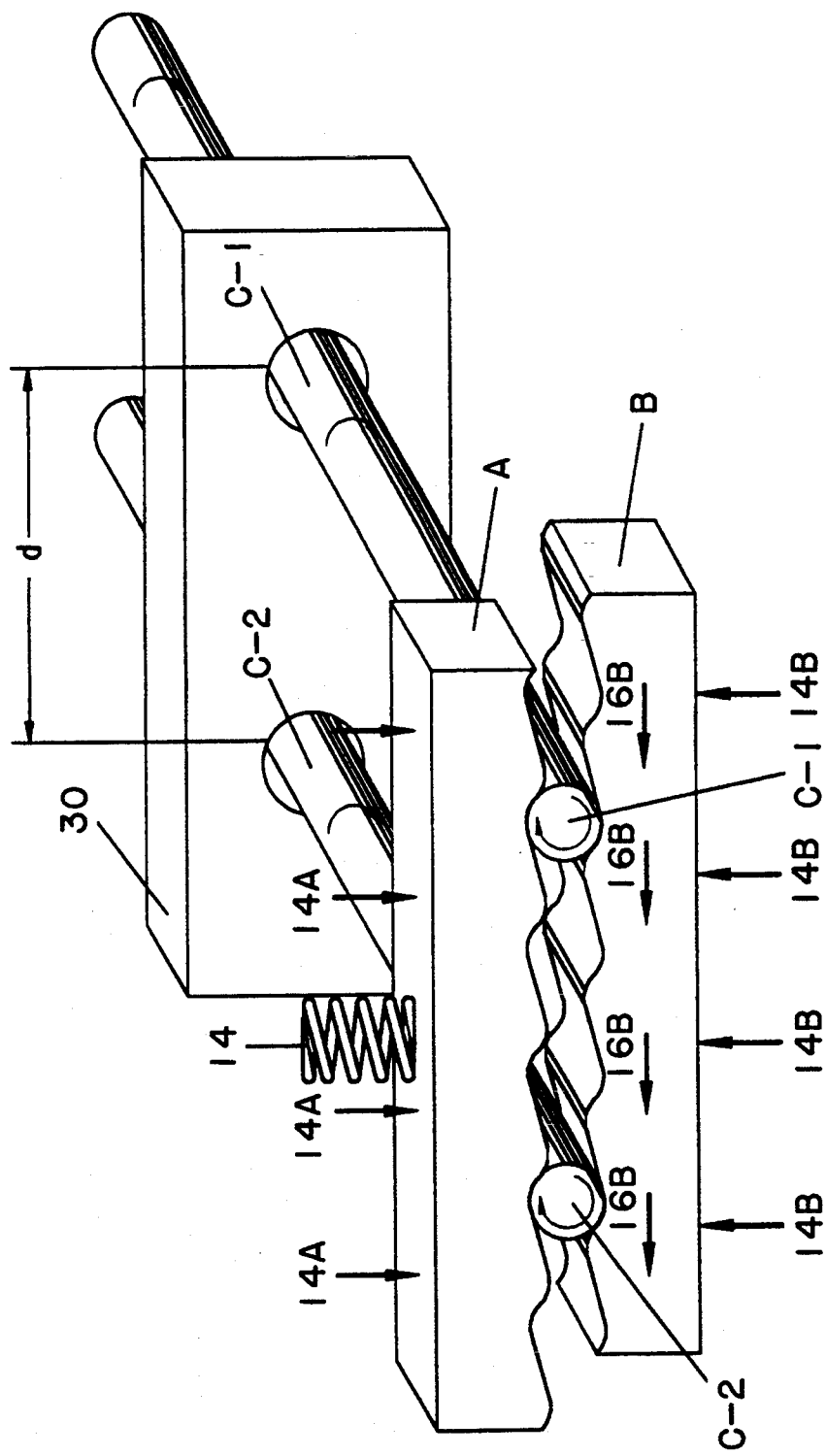

FIG. 3 schematically illustrates the operation of the invention over a two cycles in smaller increments than the showing of FIG. 2. These increments are measured in eleven successive steps from a starting position 3-1 to an ending position 3-11. Subfigure 3-1 replicates the showing in FIG. 1, where the roller C is in two confronting dwells B2 and A2. Subfigure 3-2 shows the next-following position in which the roller has started to "roll" up the slopes 24 and 26 toward the wave peaks PA2 and PB2, and the members A and B are starting to spread apart. In the next subfigures 3-3 and 3-4 this action is continued, the members A and B being spread further and further apart as the roller approaches the peaks PA2 and PB2. FIG. 3-4 replicates the position that is shown in FIG. 2. In FIG. 3-6 the roller has passed these peaks and is progressing down relatively steeper slopes 34 and 36 toward dwells A3 and B3, which are the next-successive dwells to the dwells A2 and B2 from which the roller started in FIG. 3-1. Since the steeper slopes 34 and 36 are shorter than the more gradual slopes 24 and 26, respectively, this portion of the complete cycle is shorter than the first portion, as appears in FIG. 3-6. In the latter, the roller C is just leaving the next two confronting dwells A3 and B3, after the first cycle has been completed. At this point the driving member B and the driven member A have been forced closer to each other by the compressive force represented by the arrows 14A and 14B and the driving member B has regained torque control over the driven member A, and the torque driving cycle has begun again. Subfigures 3-7 and 3-8 show the roller C approaching the successive wave peaks PB3 and PA3, and subfigures 3-9 shows the roller C between those peaks, at which moment the driving member again has reached a position of torque limit between two confronting peaks PA3 and PB3 in which it no longer drives the driven member A. Subfigures 3-10 and 3-11 show the roller C approaching and reaching, respectively, the next successive dwells A4 and B4 where driving control over driven member A is regained by driving member B.

The single anti-friction roller C shown in FIGS. 1, 2 and 3 is sufficient to illustrate how the invention works. In practice it is preferred to use a plurality of anti-friction rollers, most preferably one roller for each cycle of the confronting wave configurations. FIG. 4 schematically illustrates a preferred embodiment of the invention. To simplify the illustration only two rollers C-1 and C-2 are shown, spaced two wavelengths apart between the driving member B and the driven member A. A coil spring 14 is illustrated as a means to apply compressive force represented by the arrows 14A. The rollers are loosely held in a cage 30 which permits them to turn around their respective axes but holds the spatial distance "d" between their axes fixed at two wavelengths. It will be understood that additional rollers, not illustrated, can be added, one for each wavelength, and that the cage can provide a socket for each of them.

Figure 6:
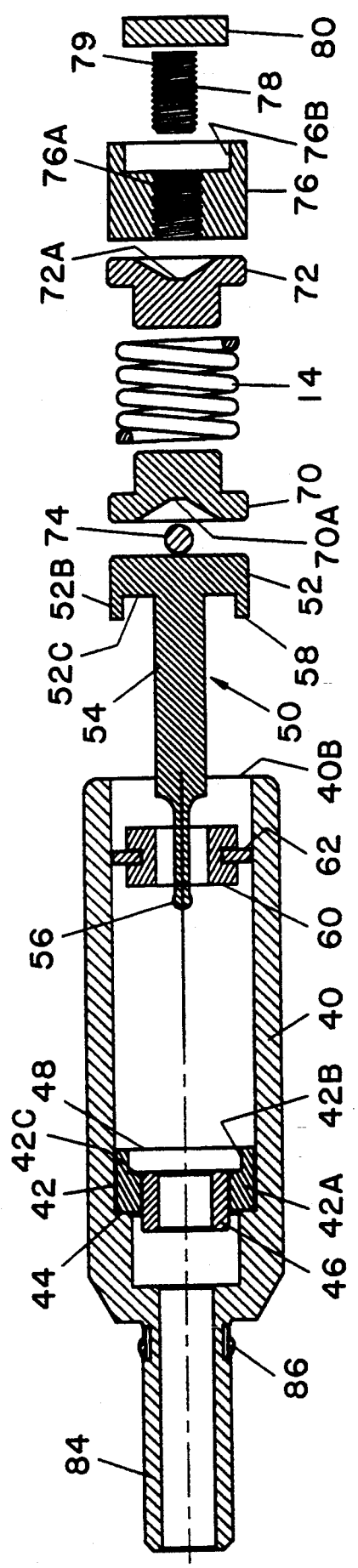
Figure 6A:
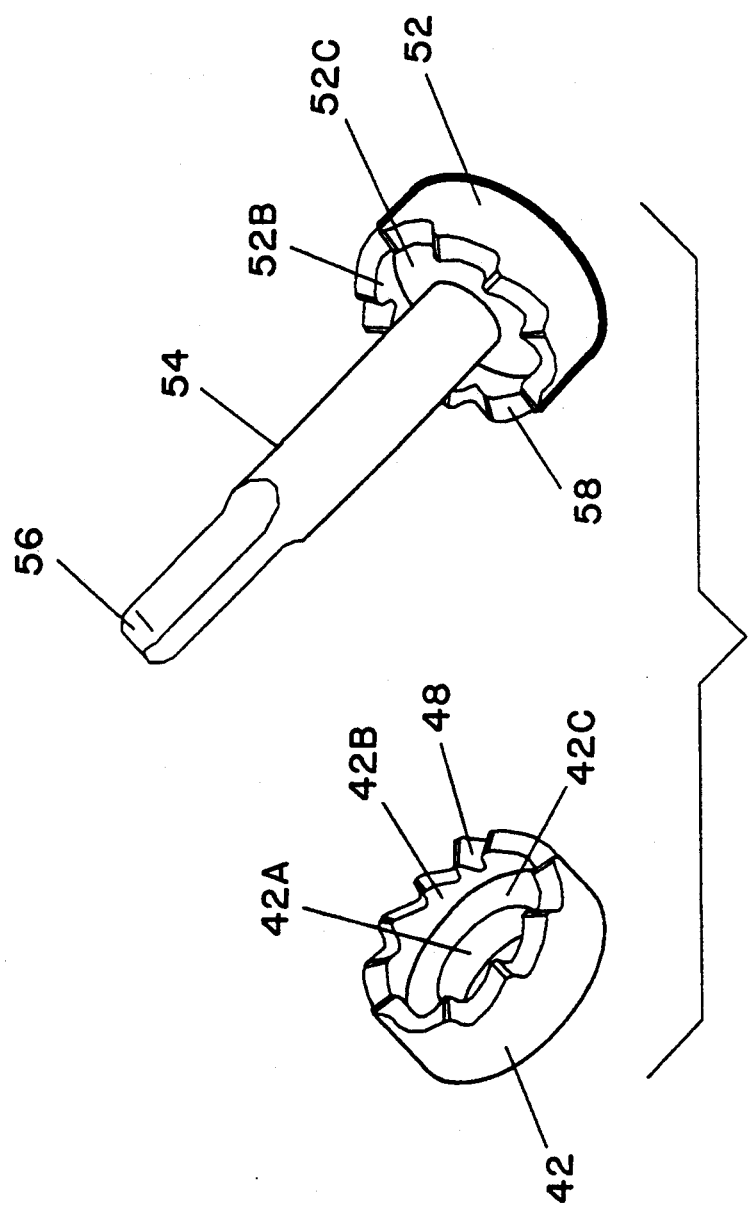
FIG. 6A is a further exploded view showing certain components of FIG. 6 in detail.

A practical embodiment of the invention, which has been devised for use in dentistry, is illustrated in FIGS. 5 and 5A assisted by FIGS. 6 and 6A. A hollow round housing 40 encloses all the parts of the clutch mechanism. The driving member 42 is annular in form and it is fixed in the housing where it rests on a shelf 44. The driving member has a main annular body portion 42A in which a sleeve bearing 46 is fitted, and a thinner annular coronal portion 42B having the same outer diameter as the main body portion 42A and forming an interior shelf 42C with the main body portion. The wave configuration of the driving member 42 is carried on the annular coronal surface 48 (shown in FIGS. 6 and 6A). The driven member 50 has a main body 52 of cylindrical outer shape dimensioned to fit within the housing 40, and bearing a coronal portion 52B which confronts the coronal portion 42B of the driving member. The wave configuration of the driven member is carried on the annular surface 58 of the driven member. A drive shaft 54 having a coupling element 56 is axially integral with, or affixed to, the driven member, for driving a tool through the torque-limiting clutch as will presently be explained. A hollow cylindrical cage 60 holds a plurality of rollers 62 between the confronting coronal surfaces 48 and 58. The cage 60 rests at one end on the shelf 42C in the driving member and at the other end in the annular space 52C between the coronal portion 52B and the drive shaft 54 of the driven member 52.

Compressive force to hold the driving and driven members together is applied by a spring 14 that is fitted between two end blocks 70 and 72, which as here illustrated are identical, each having a depression 70A and 72A, respectively, in its outer surface. An anti-friction ball bearing 74 is held in the depression 70A between the driven member and the block 70 confronting it. A closure block 76 is fitted tightly into the remote end 40B of the housing 40, compressing the spring 14 on the shelf 44 with the clutch components between them. This closure block may be used to apply an initial compressive force to the driving and driven members of the clutch. The closure block 76 has an internally-threaded bore 76A into which an adjusting screw 78 is threaded. This adjusting screw is advanced into the depression 72A in the spring block 72 confronting the closure block, for adjusting the magnitude of the compressive force of the spring 14. A wrench socket 79 is provided in the free end of the adjusting screw for this purpose. In assembling the parts of the clutch the closure block may be used to apply an initial compressive force to the spring 14, and the spring may be used to increase that force by a desired increment, or the closure block may leave the spring unloaded and the screw may be used to apply and adjust the entire compressive force. In either case, the screw is used to adjust the torque limit of the clutch. After this adjustment has been made, a cover disc 80 is fitted into a recess 76B surrounding the bore 76A to cover the screw 78 and prevent tampering with it. The value of the torque limit set into the clutch may be entered on this disc. For convenience of dentists using it, values such a 10 Ncm., 20 Ncm., and 32 Ncm., are presently in use.

As appears in FIGS. 5 and 5A the shaft 54 of the driven member 50 fits coaxially within the cage 60 and the sleeve 46, within which it is free to rotate. When the housing 40 is turned on the common axis of these parts the driving member 42 turns with it and, by its clutch action turns the driven member 50 against a resisting load that may be coupled to the coupling element 56. The housing has a tubular extension 84 surrounding the coupling element, and bears an annular resilient latch 86 around it at the junction with the housing. FIGS. 7 and 7A show how these parts may be coupled to a standard dental hand tool 90 having a tubular housing 92 and axially within it a driving shaft 94. The extension 84 fits within the tool housing 92 and around the driving shaft 94. An annular recess 96 within the tool housing near its open end 92A receives the latch 86 to removably retain the clutch housing 40 attached to the dental tool. The tool's driving shaft 94 has a slot 98 in its end for receiving the coupling element 56 of the clutch. To facilitate engagement and removal of the clutch the coupling element is made thinner than the width of the slot 98 and a ball-like expansion 56A is provided for secure engagement of the coupling element in the slot with low insertion and removal friction. The slot 98 is deeper than the length of the coupling element 56, which accordingly does not reach to the bottom of the slot. Any shock that might be imposed on the coupling element at the torque limit, when the driving and driven members move closer together, would tend to be parallel to the long axis of the coupling element 56, and therefore would not be transmitted to the tool's driving shaft 94.

The parts of the torque-limiting clutch show in FIGS. 6 and 7 are all made of materials that can be sterilized for dental or medical use, such as stainless steel. The clutch shown in this embodiment of the invention can be autoclaved. It is rugged, reliable, accurate and suitable for dental and medical uses. It is small, portable, and requires no external source of power. The spring 14 may desirably be a helical spring made of type 302 stainless steel which is stable in compression/tension up to a maximum temperature of 550° F. The clutch is intended to be autoclavable at a temperature up to 280° F., so that autoclaving will not affect its accuracy.

Figure 8:
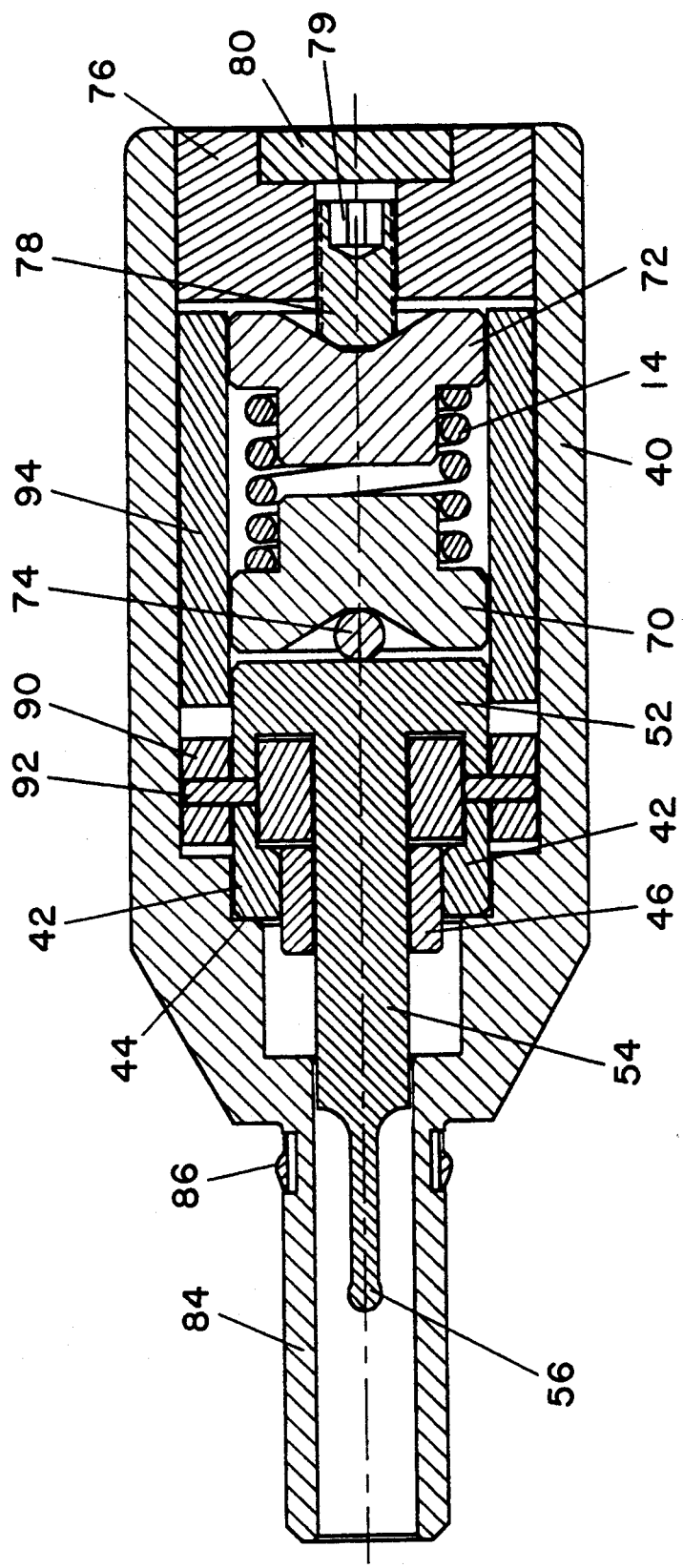

The size of the roller bearing cage 60 located within the coronal portions of the driving and driven members 42 and 50 is limited in this practical embodiment of the invention, so that the cage can support only enough roller bearings 62 to supply one bearing for each two wave cycles, as is shown in FIG. 4. FIG. 8 illustrates a second embodiment of the invention employing an external cage 90 which can be made relatively larger, for supporting additional roller bearings 92. To accommodate the larger cage the housing 40' is made larger in internal diameter than the housing 40 shown in FIG. 5, and a filler sleeve 94 is provided to center the end blocks 70 and 72 for the spring 14 and the main body 52 of the driven member 50. All other components of the embodiment shown in FIG. 8 are like the corresponding components of the embodiment shown in FIG. 5 and bear the same reference characters. With the larger bearing cage 90 it is possible to include a roller bearing 92 for each wave cycle of the clutch mechanism. An advantage is greater precision in fixing the torque limit.

We claim:

1. A torque limiting clutch comprising a driving member and a driven member each with a confronting surface and means to apply prescribed compressive force to said members to urge said confronting surfaces together, each confronting surface having on it a periodic wave of like frequency to the other confronting surface in which the wave pattern of each cycle has an up-slope rising gradually at a first slope angle from its dwell to a peak followed by a return slope falling at a second steeper slope angle to the dwell at the beginning of the next-following up-slope, said waves being in an initial spatial relation with respective dwells aligned in pairs substantially opposite each other throughout said confronting surfaces when said members are at rest, and means to apply a driving force to said driving member substantially parallel to said confronting surfaces so as to urge the up-slopes of one of said surfaces to pass by the up-slopes of the other of said surfaces toward the respective peaks of said cycles and thereby gradually increasing the magnitude of said spatial relation against said compressive force to a maximum spatial distance between said members when said peaks confront each other, said initial spatial relation being restored by said compressive force when said peaks pass each other, each of said members having a substantially flat surface at the peak of each cycle, said flat surfaces of each member lying in the locus of a common plane, said planes being substantially parallel to each other, said flat surfaces substantially confronting each other at said maximum spatial distance.

2. A torque limiting clutch according to claim 1 in which said dwells between each of said return slopes and said up-slopes are curved to receive a substantially cylindrical roller.

3. A torque limiting clutch according to claim 2 including anti-friction rollers between confronting pairs of said dwells for establishing said initial spatial relation, said rollers being located between opposing pairs of said flat surfaces at said maximum spatial distance.

4. A torque limiting clutch according to claim 1 including means to adjust the magnitude of said compressive force.

5. A torque limiting clutch according to claim 1 including anti-friction means between said confronting surfaces establishing said initial spatial relation.

6. A torque limiting clutch according to claim 5 in which said anti-friction means comprises essentially an individual rolling element between a pair of opposing dwells when said members are at rest.

7. A torque limiting clutch according to claim 6 including a plurality of said rolling elements, each between an individual pair of said opposing dwells.

8. A torque limiting clutch according to claim 7 including cage means fixing said elements each one or more unit wavelengths from each of the others.

9. A torque limiting clutch according to claim 1 in which each of said driving and driven members is substantially a right circular cylinder and each of said confronting surfaces is a circle whose plane is perpendicular to the axis of the cylinder, said periodic wave on each of said members consisting essentially of a unitary number of periods in an annular array, each of said arrays having the same number of periods.

10. A torque limiting clutch according to claim 9 in which said driving member has a central axial passage through it and said driven member has an elongated coupling member extending substantially axially from its confronting surface through said passage for coupling said torque limiter to an article to be driven.

11. A torque limiting clutch according to claim 10 including a substantially tubular housing which is open at one end, means to fix said driving member in said open end with said driving means confronting surface oriented toward the interior of said housing, and means to support said driven member in said housing with said coupling member extending toward the outside of said housing through said open end.

12. A torque limiting clutch according to claim 11 including means within said housing to apply said compressive force to said driven member.

13. A slipping clutch comprising a rotatable driving member having a face with wavelike contours thereon, a rotatable driven member having a face with wavelike contours thereon similar to the contours on the driving member face, a bore through a first of said members, said bore aligned on the axis of rotation of said first member, support means for holding said members with said faces confronting each other, said first member being fixed in said support means, the second of said members having an elongated shaft fixed at one end of said face of said second member on its axis of rotation, said second member being axially movable in either direction in said support means with said shaft extending from said second member out of said support means through said bore, and means resident in said support means for applying a predetermined force for urging said second member toward face-to-face contact with said first member.

14. A clutch according to claim 13 in which each of said faces has on it a periodic wave of like frequency to the other in which the wave pattern of each cycle has an up-slope rising gradually from its dwell to a peak followed by a return slope falling to the dwell at the beginning of the next-following cycle.

15. A clutch according to claim 14 in which said members have an initial spatial relation with respective wave pattern dwells of each aligned in pairs substantially opposite each other throughout said respective faces when said members are at rest, and a torque force applied via said support means is applied to rotate said driving member around said axis with respect to said driven member in a direction to urge the up-slopes of one of said surfaces to pass by the up-slopes of the other of said surfaces so as to bring the wave pattern peaks of each into alignment in pairs substantially opposite each other throughout said respective faces when said torque force reaches said present limit, thereby to increase the distance between said members along said axis against said compressive force.

16. A clutch according to claim 14 having a substantially flat surface at the peak of each cycle, said flat surfaces of each member lying in the locus of a common surface that is symmetrical around said axis.

17. A clutch according to claim 16 in which each of said common surfaces is a plane perpendicular to said axis.

18. A clutch according to claim 13 including means to adjust the magnitude of said force.

19. A clutch according to claim 15 including anti-friction means between said confronting surfaces establishing said initial spatial relation.

20. A clutch according to claim 19 in which said anti-friction means comprises essentially an individual rolling element between a pair of opposing dwells when said members are at rest.

21. A clutch according to claim 20 including a plurality of said rolling elements, each between an individual pair of said opposing dwells.

22. A clutch according to claim 21 including cage means fixing said elements each one or more unit wavelengths from each of the others.

23. A clutch according to claim 21 having a substantially flat surface at the peak of each cycle, said flat surfaces of each cycle lying in the locus of a common surface symmetrical around said axis so that when said peaks confront each other in opposing pairs each of said rolling elements will be located between two of said flat surfaces.

24. A clutch according to claim 13 in which each of said driving and driven members is substantially a right-circular cylinder.

25. A clutch according to claim 24 in which each of said confronting faces is a circle of revolution symmetrical around said axis.

26. A clutch according to claim 14 in which each of said driving and driven members is substantially a right-circular cylinder and each of said confronting faces is a circle of revolution around said axis, and said periodic array of each of said faces consists essentially of a unitary number of periods in an annular array, each of said arrays having the same number of periods.

27. A clutch according to claim 14 in which said return slopes in said wave patterns are steeper that said up-slopes.

28. A torque-limiting clutch comprising a driving member and a driven member each with a confronting surface, said members being rotatable around a common axis, and means to apply prescribed force parallel to said axis to said members to urge said confronting surfaces together, each confronting surface having on it a periodic wave of like frequency to the other confronting surface in which the wave pattern of each cycle has an up-slope rising gradually at a first slope angle from its dwell followed by a return slope falling at a second steeper slope angle to the dwell at the beginning of the next-following up-slope.

29. A torque-limiting clutch according to claim 28 in which said waves are in an initial spatial relation with respective dwells aligned in pairs substantially opposite each other throughout said confronting surfaces when said members are at rest, and including means to apply torque force to drive said driving member substantially parallel to said confronting surfaces so as to urge the up-slopes of one of said surfaces to pass by the up-slopes of the other of said surfaces toward the respective peaks of said cycles and thereby gradually increasing the magnitude of said spatial relation against said force to a maximum spatial distance between said members when said peaks confront each other, said initial spatial relation being restored by said force when said peaks pass each other.

30. A torque-limiting clutch according to claim 28 having a substantially flat surface at the peak of each cycle, said flat surfaces of each member lying in the locus of a common plane, said planes being substantially parallel to each other.

31. A torque-limiting clutch according to claim 28 including means to adjust the magnitude of said force.

32. A torque-limiting clutch according to claim 28 including anti-friction means between said confronting surfaces.

33. A torque-limiting clutch according to claim 32 in which said anti-friction means comprises essentially an individual rolling element between a pair of opposing dwells.

34. A torque-limiting clutch according to claim 33 including a plurality of said rolling elements, each between an individual pair of said opposing walls.

35. A torque-limiting clutch according to claim 34 including cage means fixing said elements each one or more unit wavelengths from each of the others.

36. A torque-limiting clutch according to claim 28 in which each of said driving and driven members is substantially a right circular cylinder and each of said confronting surfaces is a circle of revolution substantially perpendicular to the axis of the cylinder, said periodic wave on each of said surfaces consisting essentially of a unitary number of periods in an annular array.

37. A torque-limiting clutch according to claim 36 in which each of said arrays has the same number of periods.

38. A torque-limiting clutch according to claim 36 in which said driving member has a central axial passage through it and said driven member has an elongated coupling member extending substantially axially from its confronting surface through said passage for coupling said clutch to an article to be driven.

39. A torque-limiting clutch according to claim 38 including a substantially tubular housing which is open at one end, means to fix said driving member in said open end with its confronting surface oriented toward the interior of said housing, and means to support said driven member in said housing with said coupling member extending toward the outside of said housing through said open end.

40. A torque-limiting clutch according to claim 39 including means within said housing to apply said force to said driven member.

41. A torque-limiting clutch according to claim 40 wherein said housing includes means to adjust the magnitude of said force.

* * * * *